United States Patent
Hsiao et al.

(10) Patent No.: US 8,551,740 B2
(45) Date of Patent: Oct. 8, 2013

(54) BIOREACTOR AND METHOD FOR PRODUCING MICROBIAL CELLULOSE

(75) Inventors: Hsu-Chou Hsiao, Chiayi (TW); Ting-Sheng Lu, Hsinchu (TW); Han-Ken Chen, Hsinchu (TW); Jinn-Tsyy Lai, Hsinchu (TW); Fwu-Lin Lee, Hsinchu (TW); Chung-Liang Chu, Taichung (TW); Chii-Cherng Liao, Taipei (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 13/332,523

(22) Filed: Dec. 21, 2011

(65) Prior Publication Data

US 2012/0094334 A1    Apr. 19, 2012

Related U.S. Application Data

(62) Division of application No. 12/461,280, filed on Aug. 6, 2009, now abandoned.

(30) Foreign Application Priority Data

Jun. 11, 2009  (TW) .............................. 98119600 A

(51) Int. Cl.
*C12P 19/04* (2006.01)
*C12M 1/10* (2006.01)
*C12M 1/14* (2006.01)

(52) U.S. Cl.
USPC ..................... 435/101; 435/298.2; 435/299.1

(58) Field of Classification Search
USPC .......... 435/101, 298.2, 299.1, 299.2; 210/619
See application file for complete search history.

(56) References Cited

U.S. PATENT DOCUMENTS

| | | | | |
|---|---|---|---|---|
| 3,853,712 A | * | 12/1974 | House et al. ................ | 435/293.2 |
| 4,317,886 A | * | 3/1982 | Johnson et al. ............ | 435/299.2 |
| 5,246,854 A | * | 9/1993 | O'Brien et al. ............ | 435/286.5 |
| 6,071,727 A | * | 6/2000 | Bungay et al. ................ | 435/101 |

OTHER PUBLICATIONS

Sattler et al. "Production and Application of Bacterial Cellulose." Zentralbl. Mikrobiol., vol. 145 (1990), pp. 247-252.*

* cited by examiner

*Primary Examiner* — William H Beisner
(74) *Attorney, Agent, or Firm* — Bacon & Thomas, PLLC

(57) ABSTRACT

A technique for producing microbial cellulose is provided, including: preparing a liquid medium for microbial cultivation in a container; horizontally rotating multiple hollow tubes that are fitted together or separated from one another, so that each of the hollow tubes is alternately partially immersed in the liquid medium and partially exposed above the horizontal surface of the liquid medium; wherein each of the hollow tubes has a rough outer surface and a smooth inner surface, so as to allow microorganisms to form microbial cellulose on the outer surface of each hollow tube, as well as forming sheets of microbial cellulose on the horizontal surface of the liquid medium not being disturbed by the hollow tubes, and removing the microbial cellulose from the outer surfaces of the hollow tubes in order to obtain tubular microbial cellulose. In addition, the sheets of microbial cellulose are also harvested from the liquid medium.

13 Claims, 3 Drawing Sheets

BIOREACTOR AND METHOD FOR PRODUCING MICROBIAL CELLULOSE

This application is a divisional application of U.S. patent application Ser. No. 12/461,280, filed Aug. 6, 2009, now abandoned (of which the entire disclosure of the pending, prior application is hereby incorporated by reference).

FIELD OF THE INVENTION

The present invention relates to a bioreactor and method for producing microbial cellulose, and more particularly to a bioreactor and method for simultaneously producing tubular microbial cellulose and sheets of microbial cellulose.

DESCRIPTION OF PRIOR ART

A number of bacteria, and particularly strains of *Acetobacter*, can be cultivated to produce bacterial cellulose. In the presence of sugar and oxygen, cells of *Acetobacter* synthesize cellulose extracellularly in the form of fibrils attached to the cell. The fibrils produced by cells incubated in a static culture intertwine with one another to form a hydrophilic network known as a pellicle. This pellicle forms on the air/liquid interface of the motionless and undisturbed culture which is usually contained in shallow trays. Coherent gel-like microbial cellulose pellicles have many uses such as in wound dressings, paper, cosmetics and speaker vibration membranes, after removal of the cells.

Conventionally, the production of bacterial pellicle is carried out under the condition of static cultivation, which is not only laborious but time-consuming. In U.S. Pat. No. 6,071,727, a rotary disk bioreactor used for producing pellicular microbial cellulose is disclosed; the bioreactor includes a trough holding a liquid medium for microbial cultivation at bottom thereof; a shaft, and a series of parallel circular disks mounted on the shaft; in which an outer portion of each of the circular disks are immersed under the horizontal surface of the liquid medium, and the disks have the appropriate mesh size that would allow both the attachment and growth of microbial cellulose producing organisms, so as to allow the organisms to synthesize microbial cellulose extracellularly. The bioreactor further includes a rotating device attached to the shaft in order to rotate the disks. Therefore, when the rotating device is activated, the outer portions of the disks are alternately immersed under the horizontal surface of the liquid medium.

Pellicles of tubular microbial cellulose are produced according to special needs, such as the making of artificial blood vessels. WO 2007/093445 A1 discloses a hollow module for this purpose, which comprises two glass half-tubes; a glass cylinder, and two O-shaped rings; wherein the two glass half-tubes are mounted onto the glass cylinder by the use of the two O-shaped rings, so that an annular space is formed between them, and an upper slit and a lower slit are also formed between the two glass half-tubes; the upper slit, the lower slit, and the annular space are interconnected. The lower slit is allowed to contact a pellicular microbial cellulose grown over the horizontal surface of a microbial cultivation liquid medium, so that the microbial cellulose grows into the lower slit, the annular space, and the upper slit to form a tubular microbial cellulose. The first embodiment of WO 2007/093445 A1 shows that the growth of microbial cellulose over the horizontal surface of the liquid medium requires seven days, and it takes an additional two to three weeks to grow into tubular microbial cellulose (which has an inner diameter of 3 mm and an outer diameter of 4.5 mm).

In the U.S. Pat. No. 5,246,854, an attached growth biological reactor is disclosed, which comprises a horizontally disposed rigid cylinder having a sufficiently rough outer surface to allow for attachment and growth of filamentous fungi, and the cylinder is rotatable about a longitudinal axis thereof; a trough disposed below the cylinder, which includes a culture medium for at least a portion of the cylinder to be immersed therein; a blade horizontally disposed and in parallel to the cylinder, and the blade can be brought into contact with the cylinder to scrape any substances off the surface of the cylinder; and a rotating device connected to the cylinder for rotating the cylinder. Although the bioreactor can be used to produce filamentous fungi continuously, the cylinder is inadequate to be used to produce tubular microbial cellulose.

The above-mentioned patents have been included in this disclosure by reference.

Though the aforesaid patents have disclosed methods and modules for the production of tubular microbial cellulose, the production efficiency and modules can be further enhanced still. This is especially true as the requirement for larger tubular microbial cellulose increases. For example, in regard to food casing used in the food industry (especially the vegetarian casing, as the microbial cellulose is regarded as a type of vegetarian food), the current production efficiency and modules have been found to lag behind the actual requirements from the industry.

SUMMARY OF THE INVENTION

A primary objective of the present invention is to provide a novel module for producing tubular microbial cellulose.

Another objective of the present invention is to provide a method for producing tubular microbial cellulose.

Another objective of the present invention is to provide a module for simultaneously producing tubular microbial cellulose of different diameters.

Yet another objective of the present invention is to provide a method for simultaneously producing tubular microbial cellulose of different diameters.

A further objective of the present invention is to provide a method for simultaneously producing tubular microbial cellulose and sheets of microbial cellulose.

In order accomplished the aforesaid objectives, a bioreactor for producing microbial cellulose constructed according to the present invention comprises:

a container for holding a liquid medium for microbial cultivation; and a horizontal module having hollow tubes being fitted together at an interval or separated from one another, said horizontal module being horizontally rotatably disposed in said container, so that each of said hollow tubes is alternately partially immersed in the liquid medium held in said container, and partially exposed above a horizontal surface of the liquid medium.

The present invention also provides a method for producing microbial cellulose, comprising the following steps:

preparing a liquid medium having cellulose-producing microorganisms in a container;

horizontally rotating multiple hollow tubes that are fitted together at an interval or separated from one another, such that each of the hollow tubes is alternately partially immersed in the liquid medium and partially exposed above the horizontal surface of the liquid medium, so as to allow the microorganisms to form microbial cellulose on an outer surface of each of the hollow tubes, as well as forming sheets of microbial cellulose on a horizontal surface of the liquid medium not being disturbed by the hollow tubes in the container; and removing the microbial cellulose from the outer surfaces of each of the hollow tubes, thereby obtaining tubular microbial cellulose; wherein each of the hollow tubes has a rough outer surface and a smooth inner surface.

The present invention has the advantages of being able to produce tubular microbial cellulose of large diameters at high production efficiency. Another advantage of the invention is that tubular microbial cellulose of different diameters can be produced simultaneously. The invention is also advantageous in that tubular microbial cellulose and sheets of microbial cellulose can be produced simultaneously.

DETAILED DESCRIPTION OF PREFERRED EMBODIMENTS

Figure 1:
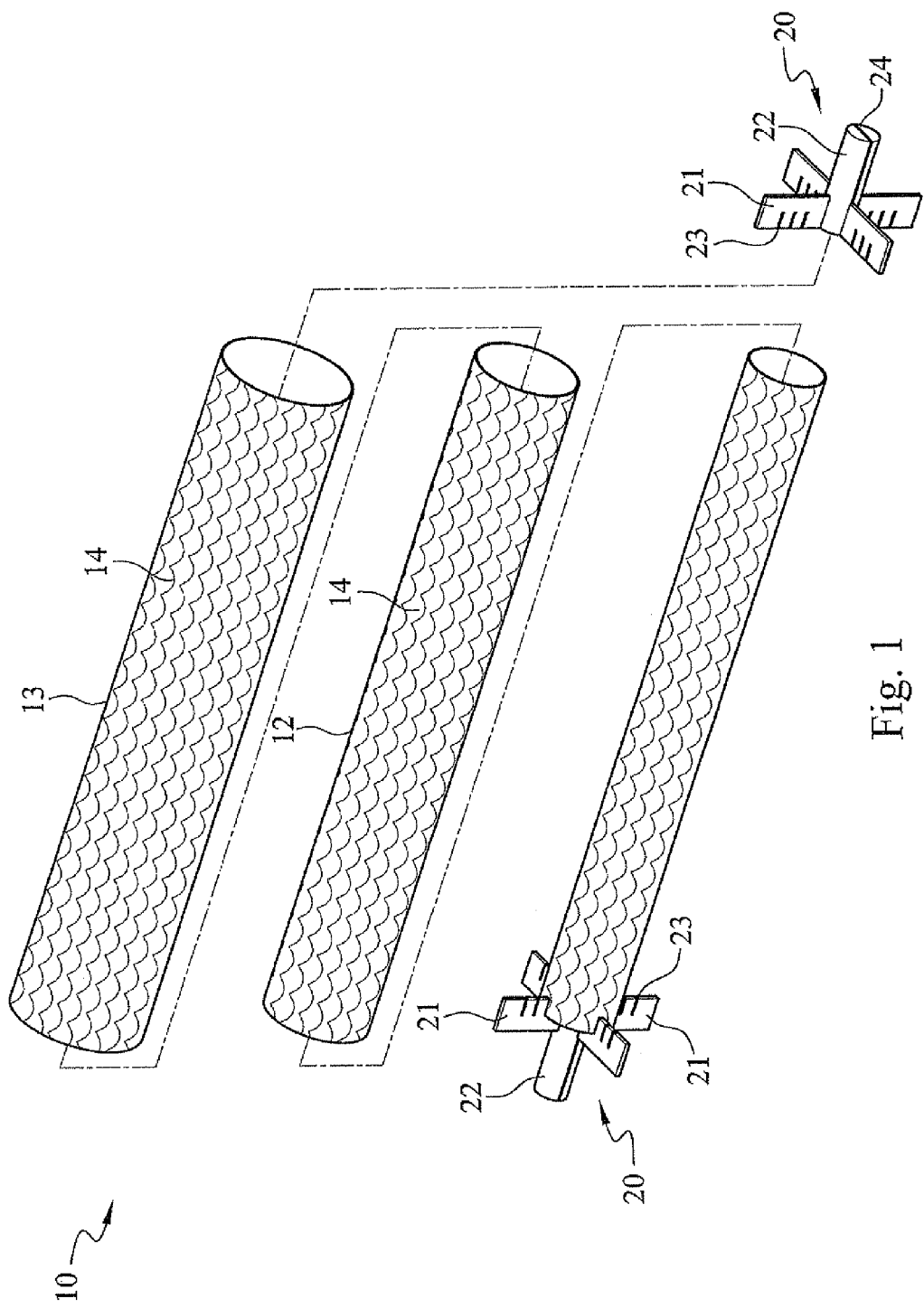
FIG. 1 is a perspective view that shows a horizontal module assembled from fitting three hollow tubes together according to a preferred embodiment of the invention.
Figure 2:
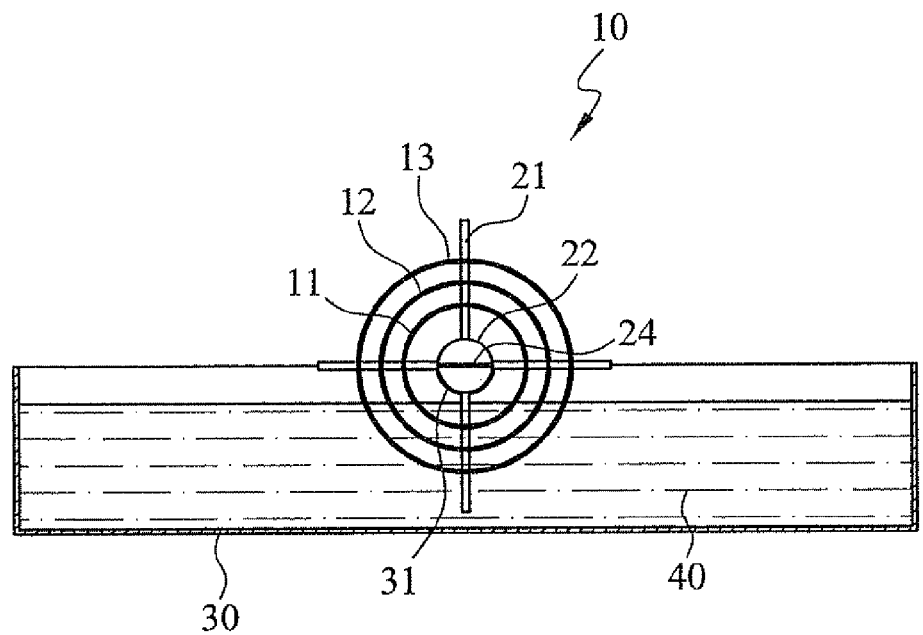
FIG. 2 is a lateral view that shows a bioreactor according to a preferred embodiment of the invention, in which the container 30 is transparent.

FIGS. 1 and 2 show a horizontal module 10 assembled by fitting three hollow tubes together according to a preferred embodiment of the invention. The horizontal module 10 includes three hollow tubes 11, 12, and 13, which have diameters of 30 mm, 40 mm, and 50 mm, respectively, and a wall thickness of 1.0 mm; and two spacers 20. Each of the spacers 20 has a cross-shaped section 21 and a shaft 22. The cross-shaped section 21 has three groups of joining clefts 23 surroundingly disposed around a central point of the cross, and each group includes four joining clefts 23 that are spaced at 5 mm from the next group of joining clefts 23. The first group of four joining clefts are disposed at 15 mm from the central point of the cross, and are used to join with and hold an end of the first hollow tube 11 (with a diameter of 30 mm); the second group of four joining clefts are disposed at 20 mm from the central point of the cross, and are used to join with and hold an end of the second hollow tube 12 (with a diameter of 40 mm); while the third group of four joining clefts are disposed at 25 mm from the central point of the cross, and are used to join with and hold an end of the third hollow tube 13 (with a diameter of 50 mm). The three hollow tubes 11, 12, and 13 have one end respectively joined with the three groups of joining clefts 23 of a first spacer 20, with an interval of 5 mm between the hollow tubes as described above. Subsequently, the same steps are repeated to have another ends of the three hollow tubes 11, 12, and 13 respectively joined with the joining clefts of a second spacer 20, with an interval of 5 mm between the hollow tubes. By assembling the components according to the aforesaid description, two shafts 22 that extend horizontally from the spacers 20 can be observed (the shafts have an identical axis of horizontal rotation), as well as the horizontal module 10 that is assembled by fitting the three hollow tubes 11, 12, and 13 together at an interval from one another.

Each of the three hollow tubes 11, 12, and 13 has a rough outer surface and a smooth inner surface. More preferably, the rough outer surface has a regular texture 14 to allow for attachment and even growth of microorganisms thereon.

Figure 3:
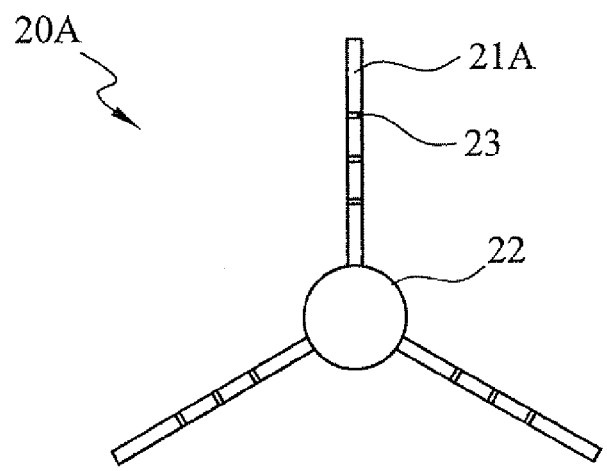
FIG. 3 is a lateral view that shows a spacer according to another preferred embodiment of the invention.

Similarly, the horizontal module 10 of FIGS. 1 and 2 can also be assembled by using a spacer 20A having a Y-shaped section 21A shown in FIG. 3. When comparing the spacer 20A with the spacer 20 of FIGS. 1 and 2, it can be observed that the only difference being that the former has a Y-shaped section 21A and the latter has a cross-shaped section 21, whereas both have identical shafts 22 and joining clefts 23.

FIG. 2 shows the horizontal module 10, as well as a container 30 holding a liquid medium 40 for microbial cultivation. The horizontal module 10 and the container 30 are the main components that make up the bioreactor for producing microbial cellulose according to the invention, in which the container 30 has two semicircular indentations 31 disposed on upper edges of both lateral sides thereof, so as to be joined with and hold the shafts 22 of the horizontal module 10. Therefore, the horizontal module 10 can be disposed in the container 30 for horizontal rotation, and each of the three hollow tubes 11-13 is alternately partially immersed in the liquid medium 40 held in the container 30, and partially exposed above the horizontal surface of the liquid medium 40. One of the shafts 22 further comprises a notch 24 at an end thereof, and the notch 24 is able to be coupled to a corresponding linear button (not shown in the drawing) of a transmission shaft, such that when the transmission shaft is driven into rotation by a motor, the horizontal module 10 of FIG. 2 is allowed to rotate horizontally.

Further variations may be applied to the bioreactor of the invention. For instance, the horizontal module 10 of FIGS. 1 and 2 can be increased to two, or the horizontal module 10 may have one or two hollow tubes added to or taken from the existing three.

Figure 4:
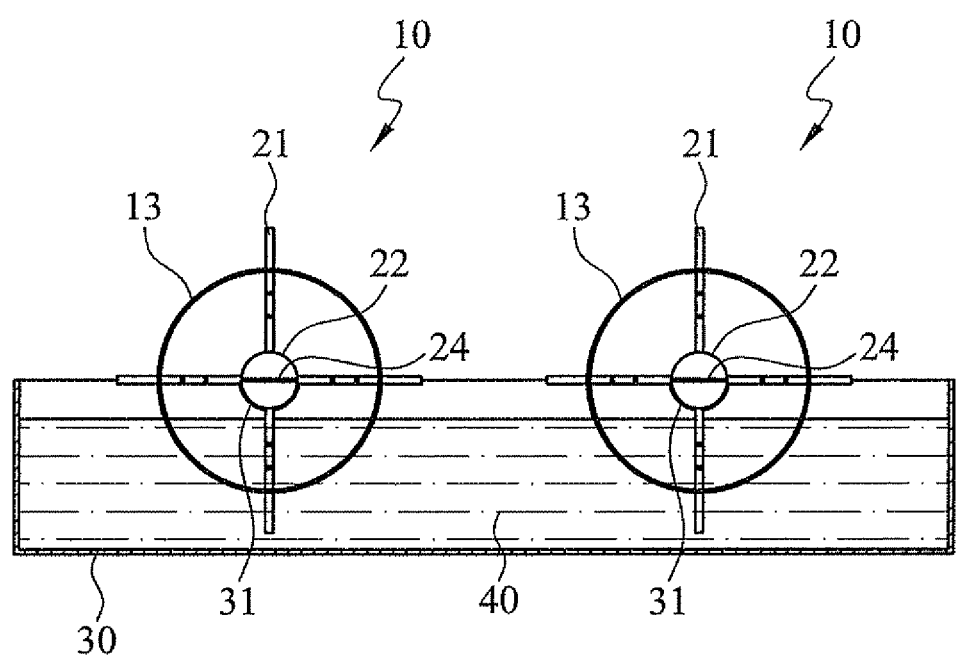
FIG. 4 is a lateral view that shows a bioreactor according to another preferred embodiment of the invention, in which the container 30 is transparent.

FIG. 4 shows a bioreactor according to another preferred embodiment of the invention, in which all of the components of the bioreactor are identical to those shown in FIG. 2, except that two horizontally separated tubes having a diameter of 50 mm are used, and the components similar to those of FIG. 2 are labeled by similar numbers and symbols.

The bioreactor of the present invention may be further comprised of a lid for covering on top of the container 30, so as to minimize contamination of the liquid medium 40 by various bacteria from the air. When a lid is included, a height of surrounding walls of the container 30 must be increased to make it higher than the highest part of the horizontal module 10, so that the lid can cover the container properly. Selectively, the bioreactor of the present invention may be placed in an environment not contaminated by various bacteria to carry out cultivation of microorganisms.

A microorganism that is adequate to be applied in the method for producing microbial cellulose according to the invention is *Gluconacetobacter xylinus*.

According to the present invention, the method for producing microbial cellulose includes the cultivation of microorganisms by using the aforesaid bioreactor of the invention, under the conditions described in prior arts (the conditions described in the patents mentioned in Background of the Invention of this disclosure, for instance). As a result, the microorganisms are allowed to form tubular microbial cellulose on the outer surfaces of each of the hollow tubes 11-13, as well as forming sheets of microbial cellulose on the horizontal surface of the liquid medium not being disturbed by the hollow tubes in the container 30. When harvesting the microbial cellulose, the horizontal module 10 is removed from the container and then disassembled. Subsequently, the hollow tubes 11-13 are separated from one another, and because the outer surfaces of the hollow tubes are rough and the inner surfaces are smooth, the microbial cellulose formed by the microorganisms predominately adhere to the rough surfaces. Therefore, the hollow tubes can be separated from one another easily, thereby resulting in hollow tubes having a layer of microbial cellulose on outer surfaces thereof, for example without having the inner surface of the outer most hollow tube 13 adhered to the microbial cellulose on the outer surface of the middle hollow tube 12, which allows the hollow tubes to be removed easily and prevents the microbial cellulose from being damaged structurally. The layer of microbial cellulose is then peeled off the outer surfaces of the hollow tubes, followed by the removal of microorganisms thereon, thereby obtaining a product of tubular microbial cellulose. Selectively, the tubular microbial cellulose may be further dried and hydrated. After removing the horizontal module 10 from the container 30, the method further comprises a step of obtaining sheets of microbial cellulose from the liquid medium 40 held in the container, and then removing the microorganisms thereon, thereby resulting in a product of sheets of microbial cellulose. Selectively, the sheets of microbial cellulose may be further dried and hydrated.

The bioreactor of the invention can not only be used to produce tubular microbial cellulose of different diameters, but also effectively reduces the cultivation time and increases the yield of microbial cellulose for every unit of time/space.

The bioreactor of the invention can not only be used to cultivate filament-producing microorganisms such as fungi and *Actinobacteria*, but also microorganisms that produce solid-state products as well. When cultivating microorganisms that need to be cultured anaerobically, the culture medium may be gently stirred to promote even mixing of the microorganisms with the medium, which consequently elevates the usage efficiency of the culture medium.

The bioreactor of the invention can be used in the production of casing applied in foods, and also further applied in the production of biomedical materials.

The present invention can be better understood by referring to following embodiments thereof; the embodiments are only intended to be used to elucidate the invention, and are not to be used to limit the scope of the invention in any ways.

Example 1

Three Hollow Tubes Fitted Together as a Group

In this example, the bioreactor shown in FIGS. 1 and 2 was used, wherein the container 30 has a length of 33 cm, a width of 23 cm, and a height of 4 cm, and the three hollow tubes 11-13 have a length of 30 cm. The shafts 22 were driven into rotation by a motor at 10 rpm. Consequently, the horizontal module 10 was rotated horizontally at 10 rpm as well.

The bioreactor was placed in an environment free of contaminating bacteria in order to carry out microbial cultivation, in which the liquid medium 40 held in the container 30 was 35 mm of height, and the culture temperature was 30° C. The liquid medium 40 was a pre-agitated culture prepared in advance. The pre-agitated culture was a liquid medium comprising the ingredients listed in the following table and 5% microorganisms, the culture was incubated free of contaminating bacteria at 120 rpm and 30° C. for two days, and was filled with *Gluconacetobacter xylinus* by the time the incubation was completed.

| | |
|---|---|
| Sucrose | 5% |
| Yeast extract | 0.5% |
| $(NH_4)_2SO_4$ | 0.5% |
| $KH_2PO_4$ | 0.3% |
| $MgSO_4 \cdot 7H_2O$ | 0.005% |

The cultivation was carried out under room temperature and normal atmospheric environment for seven days.

Overall, 1.62 g/L of sheets of bacterial cellulose was obtained from the undisturbed portion of liquid medium, and three different sizes of tubular bacterial cellulose, which weighed 1.425 g/L in total; were obtained from the horizontal module, and resulted in a total harvest of 3.045 g/L in this example.

Example 2

Two Hollow Tubes Fitted Together as a Group

The steps and the bioreactor employed in Example 1 were also used in this embodiment, except that the second hollow tube (with a diameter of 40 mm) from the three hollow tubes was not used.

Overall, 1.745 g/L of sheets of bacterial cellulose was obtained from the undisturbed portion of liquid medium, and two different sizes of tubular bacterial cellulose, which weighed 1.815 g/L in total; were obtained from the horizontal module, and resulted in a total harvest of 3.56 g/L in this example.

Example 3

A Single Hollow Tube

The steps and the bioreactor employed in Example 1 were again used in this embodiment, except that the first and the second hollow tubes (with a diameter of 30 mm and 40 mm, respectively) from the three hollow tubes were not used.

In this example, 1.745 g/L of sheets of bacterial cellulose was obtained from the undisturbed portion of liquid medium, and one tubular bacterial cellulose, which weighed 0.77 g/L in total; was obtained from the horizontal module, and resulted in a total harvest of 2.515 g/L.

Example 4

Two Separated Hollow Tubes

The steps and the bioreactor employed in Example 3 were used in this embodiment, except that two separated hollow tubes with a diameter of 50 mm positioned in parallel to each other were used. The two separated and parallel hollow tubes were kept from each other at a minimal distance of 65 mm.

Overall, 2.15 g/L of sheets of bacterial cellulose was obtained from the undisturbed portion of liquid medium, and two tubular bacterial cellulose products, which weighed 2.255 g/L in total; were obtained from the horizontal module, and resulted in a total harvest of 4.405 g/L in this embodiment.

| g/L | Three Hollow Tubes Fitted Together (50 mm + 40 mm + 30 mm) | Two Hollow Tubes Fitted Together (50 mm + 30 mm) | One Single Hollow Tube (50 mm) | Two Separated Hollow Tubes (2 × 50 mm) |
|---|---|---|---|---|
| Tubular | 1.425 | 1.815 | 0.77 | 2.255 |
| Sheets | 1.62 | 1.745 | 1.745 | 2.15 |
| Total | 3.045 | 3.56 | 2.515 | 4.405 |

The table above lists the total yields of microbial cellulose from Examples 1-4, which shows that the yield of microbial cellulose is the highest when two separated hollow tubes are used in the cultivation. The inventors deduce that a possible reason for the results is that two separated hollow tubes could produce stronger disturbances onto the liquid medium, which leads to more even distribution of the microorganisms in the liquid medium held in the container, and thus the usage efficiency of the liquid medium is higher than in other cases. Unexpectedly, the tubular bacterial cellulose yield per unit of hollow tube from Example 4 (two separated hollow tubes) is threefold that of Example 3 (a single hollow tube), instead of the predicted twofold.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A method for simultaneously producing tubular microbial cellulose of different diameters, comprising the following steps:
    preparing a liquid medium having cellulose-producing microorganisms in a container;
    horizontally rotating multiple hollow tubes that are fitted together concentrically at an interval from one another, such that each of the hollow tubes is alternately partially immersed in the liquid medium and partially exposed above the horizontal surface of the liquid medium, so as to allow the microorganisms to form microbial cellulose on an outer surface of each of the hollow tubes, as well as forming sheets of microbial cellulose on a horizontal surface of the liquid medium not being disturbed by the hollow tubes in the container; and
    removing the microbial cellulose from the outer surfaces of each of the hollow tubes, to simultaneously obtain tubular microbial cellulose of different diameters; wherein each of the hollow tubes has a rough outer surface and a smooth inner surface.

2. The method of claim 1, wherein the microorganisms are *Gluconacetobacter xylinus*.

3. The method of claim 1, wherein the rough outer surface has a regular texture.

4. The method of claim 1, wherein the hollow tubes are 2-5 cylindrical tubes.

5. The method of claim 4, wherein the inner most tube of the hollow tubes has a diameter of 1-5 cm, and the interval between two neighboring hollow tubes is 0.5-2 cm.

6. The method of claim 1 further comprising a step of removing sheets of microbial cellulose from the liquid medium in the container.

7. A method for producing simultaneously sheets and tubes of microbial cellulose of different diameters, comprising the following steps:
    preparing a liquid medium having cellulose-producing microorganisms in a container;
    horizontally rotating multiple hollow tubes that are fitted together concentrically at an interval from one another, such that each of the hollow tubes is alternately partially immersed in the liquid medium and partially exposed above the horizontal surface of the liquid medium, so as to allow the microorganisms to form microbial cellulose on an outer surface of each of the hollow tubes, as well as forming sheets of microbial cellulose on a horizontal surface of the liquid medium not being disturbed by the hollow tubes in the container; and
    removing the microbial cellulose from the outer surfaces of each of the hollow tubes, to simultaneously obtain sheets and tubular microbial cellulose of different diameters; wherein each of the hollow tubes has a rough outer surface and a smooth inner surface.

8. The method of claim 7, wherein the microorganisms are *Gluconacetobacter xylinus*.

9. The method of claim 7, wherein the rough outer surface has a regular texture.

10. The method of claim 7, wherein the hollow tubes are 2-5 cylindrical tubes.

11. The method of claim 10, wherein the inner most tube of the hollow tubes has a diameter of 1-5 cm, and the interval between two neighboring hollow tubes is 0.5-2 cm.

12. The method of claim 7, wherein the inner most tube of the hollow tubes has a diameter of 1-5 cm, and the interval between two neighboring hollow tubes is 0.5-2 cm.

13. The method of claim 7 further comprising a step of removing sheets of microbial cellulose from the liquid medium in the container.

\* \* \* \* \*